(12) United States Patent
Kostamo et al.

(10) Patent No.: US 11,738,121 B2
(45) Date of Patent: Aug. 29, 2023

(54) BIOCOMPATIBLE MEDICAL DEVICE VISIBLE IN X-RAY AND METHOD FOR MANUFACTURING THEREOF

(71) Applicant: Picosun Oy, Espoo (FI)

(72) Inventors: Juhana Kostamo, Vantaa (FI); Mikko Matvejeff, Espoo (FI); Xiaopeng Wu, Helsinki (FI)

(73) Assignee: PICOSUN OY, Espoo (FI)

( * ) Notice: Subject to any disclaimer, the term of this patent is extended or adjusted under 35 U.S.C. 154(b) by 499 days.

(21) Appl. No.: 16/832,518

(22) Filed: Mar. 27, 2020

(65) Prior Publication Data

US 2020/0306417 A1      Oct. 1, 2020

Related U.S. Application Data

(60) Provisional application No. 62/826,568, filed on Mar. 29, 2019.

(51) Int. Cl.
| | |
|---|---|
| *A61L 29/18* | (2006.01) |
| *A61L 31/18* | (2006.01) |
| *A61L 31/08* | (2006.01) |
| *C23C 16/40* | (2006.01) |
| *C23C 16/455* | (2006.01) |
| *A61L 29/10* | (2006.01) |

(52) U.S. Cl.
CPC ............. *A61L 29/18* (2013.01); *A61L 29/106* (2013.01); *A61L 31/088* (2013.01); *A61L 31/18* (2013.01); *C23C 16/40* (2013.01); *C23C 16/45525* (2013.01); *A61L 2420/02* (2013.01)

(58) Field of Classification Search
CPC ............. A61L 2400/18; A61L 2420/02; A61L 29/106; A61L 29/18; A61L 31/088; A61L 31/18; C23C 16/40; C23C 16/405; C23C 16/45525

See application file for complete search history.

(56) References Cited

U.S. PATENT DOCUMENTS

| | | | | |
|---|---|---|---|---|
| 8,864,816 | B2 * | 10/2014 | Weber ............... | B82Y 10/00 623/1.34 |
| 2010/0274176 | A1 * | 10/2010 | Baumgart ............ | A61L 15/42 424/617 |
| 2011/0054633 | A1 * | 3/2011 | Miller ................ | A61F 2/82 623/23.72 |
| 2013/0266629 | A1 * | 10/2013 | Arvidsson ........... | A61C 8/00 424/653 |

OTHER PUBLICATIONS

Zonensain et al. (Appl Phys Lett. 2015;106:5 pages (Year: 2015).*

* cited by examiner

*Primary Examiner* — Ernst V Arnold
(74) *Attorney, Agent, or Firm* — Nixon & Vanderhye

(57) ABSTRACT

A biocompatible medical device is provided having at least one surface, wherein at least a part of this surface is coated with a biocompatible layer configured to provide visibility of the device in X-rays.

2 Claims, 1 Drawing Sheet

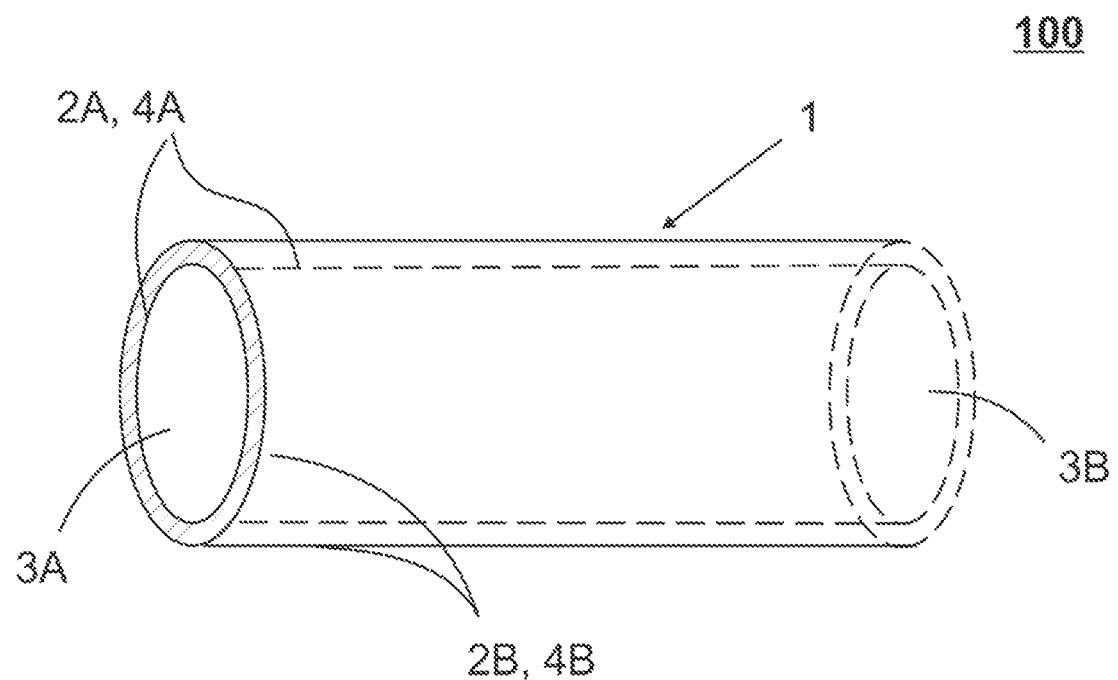

BIOCOMPATIBLE MEDICAL DEVICE VISIBLE IN X-RAY AND METHOD FOR MANUFACTURING THEREOF

FIELD OF THE INVENTION

The present invention generally relates to substrate processing methods and apparatus. More specifically, the invention relates to a biocompatible medical device visible in X-ray and a method for manufacturing thereof.

BACKGROUND OF THE INVENTION

This section illustrates useful background information without admission of any technique described herein representative of the state of the art.

There is a need for medical devices to be visible in X-ray in tomography applications, for example. An exemplary medical device of such kind is a tube used for intravenous injections, which is usually inserted under skin for the period of injection. Such tubes are typically made of thermoplastic polyurethane (TPU). After injection, a physician withdraws the tube; however, certain risk exists that a part of the tube is broken and it will remain inside the body causing infections and mechanical damages as a foreign material. To solve this problem, heavy metal powder, such as tungsten powder, can be embedded into to the tube material. Therefore, a physician could quickly check with X-ray, whether there is any risk that a part of the tube will remain inside the body. Tungsten has high absorption efficiency to X-ray and therefore it is X-ray visible, while TPU is almost transparent to X-ray radiation.

However, a fabrication process of the items containing heavy metal powder(s) must be controlled with very high accuracy, to avoid leakage of tungsten or any other heavy metal to the patient's body. The manufacturing process thus faces technical challenges, whereby the cost of a final product is also increased.

SUMMARY OF THE INVENTION

An objective of the present invention is to solve or to at least alleviate each of the problems arising from the limitations and disadvantages of the related art. The objective is achieved by various embodiments of a biocompatible medical device visible in X-ray and a method for manufacturing thereof.

In an aspect, a medical device is provided.

In embodiment, the medical device has at least one surface, wherein at least a part of said surface is coated with a biocompatible layer configured to provide visibility of said device to X-rays.

In embodiment, the biocompatible layer comprises at least one metal oxide. Use of biocompatible heavy metal oxides can be advantageous to replace dangerous metals during fabrication of any medical instruments, such as tubular items, which need to be visible to X-rays.

In embodiment, the biocompatible heavy metal oxide layer comprises one or more compound(s) selected from the group consisting of hafnium oxide ($HfO_2$), niobium (pent) oxide ($Nb_2O_5$), tungsten oxide ($WO_3$) and tantalum oxide ($TaO_x$). Mentioned layer may be formed from any other ALD deposited materials having molecular weight as high- or higher than the abovementioned oxides. Also a topmost ALD surface layer is advantageously configured biocompatible. Thus, the topmost layer can be made of the other materials than those mentioned above, such as of titanium oxide ($TiO_2$), for example. The atomic numbers of $HfO_2$ or $TaO_x$ may be great enough to interact with X-rays; therefore, the material can then be visible on an X-ray image. Alternatively or additionally to oxide compounds, carbides and nitrides can be utilized. In embodiments, these different materials can be combined together, e.g. $WO_3$ and $HfO_2$.

In embodiment, the medical device is configured as a stent, an intravenous injection tube or a catheter, such as a food catheter, for example.

In embodiment, the biocompatible layer is an Atomic Layer Deposition (ALD) layer.

Utilization of ALD technology has many benefits. The ALD film provide a conformal, uniform coverage on all surfaces of the tube or a medical instrument (e.g. on inner and outer sides), or, with a special (mask) arrangement, on one side. By provision of said uniform film, it can be ensured that the entire instrument is visible to X-ray, which eliminates the risks that parts of the instrument without X-ray sensitive material will remain in the body without being noticed.

In an aspect, a method for manufacturing a medical device is provided.

In embodiment, the method comprises: obtaining a medical device having at least one surface; and depositing a biocompatible layer on at least a part of the surface of said device by Atomic Layer Deposition (ALD), wherein said biocompatible layer is configured to provide visibility of said device to X-rays.

In the present application, the term "medical device" widely refers to intravenous injection tube, food catheter and/or any insert which is made of soft material e.g. TPU, which is not sensitive to X-ray.

In the present application, the term "X-ray" is applicable to both X-ray imaging and tomography imaging, as the latter is based on X-rays.

In the present disclosure, materials with a layer thickness below 1 micrometer (μm) are referred to as "thin films".

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which:

FIG. 1 shows a medical device, according to some exemplary embodiment.

DETAILED DESCRIPTION

Detailed embodiments of the present invention are disclosed herein with the reference to accompanying drawing. The same reference characters are used throughout the drawing to refer to same members. Following citations are used for the members:

100—a medical device;
1—a body of the medical device;
2A, 2B—internal- and external surfaces of the medical device, accordingly;
3A, 3B—apertures at the ends of the medical device;

4A, 4B—coating at the internal- and external surfaces of the medical device, accordingly.

FIG. 1 illustrates, at 100, a concept underlying a medical device according to various embodiments.

The medical device 100, hereafter, a device, comprises a body 1 with at least one surface. FIG. 1 shows a device having an interior space/volume and, therefore, an internal surface 2A and an external surface 2B. At least one aperture 3A, 3B can be arranged on at least one end of the body 1. The device 100 shown on FIG. 1 is essentially tubular having the apertures 3A, 3B at both ends of the tube. In some configurations, the body 1 is configured as a mesh tube. In various configurations, the device can be shaped as a tube, an optionally curved channel, a blind tube, a cone, a truncated cone, a box, etc. or adopt more complex shapes.

In preferred configurations, the device 100 is a stent or an intravenous injection tube.

In the device, having at least one surface, said surface is deposited, at least in part, with a coating layer 4A, 4B. The layer is preferably a biocompatible layer configured to provide visibility of said device in X-rays. The biocompatible coating layer is preferably configured as a film, preferably, a thin film having thickness of about and or more than 50 nm.

The coating layer 4A, 4B is applied with a method of chemical deposition in gaseous (vapour) phase, such as Atomic Layer Deposition (ALD) or, alternatively, Chemical Vapour Deposition (CVD). For the purposes of the present disclosure, ALD is utilized as a preferred deposition method.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process. It should be noted that with PEALD and photon-enhanced ALD, the additive treatment can be limited to the surfaces visible to the radiation source.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD deposition cycle proceeds in two half-reactions (pulse A-purge A; pulse B-purge B), whereby a (sub)layer of material is formed in a self-limiting (self-saturating) manner, typically being 0.05-0.2 nm thick. Typical substrate exposure time for each precursor ranges within 0.01-1 seconds.

Pulse A comprises a first precursor in a gaseous phase (first precursor vapour) and pulse B comprises a second precursor in a gaseous phase (second precursor vapour). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapour pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

With reference back to FIG. 1, the medical device 100 has a body made of X-ray insensitive material. In some instances, said X-ray insensitive material can be thermoplastic polyurethane (TPU), or any other appropriate material. In some further instances, mentioned material can be polylactic acid (PLLA).

The body 1 is further coated, at least partly, with said biocompatible coating provided as a single layer or as a number of layers. In embodiments, biocompatible coating is provided on an outer side and/or on an inner side of the device (the body). The biocompatible coating is configured to provide visibility (of coated parts) in X-rays.

The biocompatible layer can comprises at least one metal oxide. In embodiment, the biocompatible layer comprises at least one heavy metal oxide.

In present disclosure, by "heavy metal" we refer to metal elements heavier than selenium (Se); as in terms of atomic weight. Said (heavy) metal oxide layer comprises one or more compound(s) selected from the group consisting of $HfO_2$ and $TaO_x$. Thickness of the layer can be selected such, as to provide desired visibility of the device in X-rays. Thicker coating (e.g. 100 nm) provides a clearer image due to attenuation of X-rays after penetration into the coating layer (a film). A part of X-rays is absorbed and a detector is used to capture the change of energy attenuation and reflect such a change with grey scale.

The biocompatible coating layer is preferably provided as an Atomic Layer Deposition (ALD) layer.

The invention further pertains to a method for providing a medical device 100. The method comprises: obtaining a medical device, having at least one surface; and depositing a biocompatible layer on at least a part of the surface of said device by Atomic Layer Deposition (ALD), wherein said biocompatible layer is configured to provide visibility of said device in X-rays.

Deposition of said biocompatible layer is preferably conducted at relatively low temperature, e.g. the temperature below 150° C.

ALD is advantageously utilized hereby to deposit, inter alia, metals, metal oxides and metal carbides, wherein a metal compound can be provided as any one disclosed hereinabove. Additionally, such metals as ruthenium (Ru), platinum (Pt) and palladium (Pd), can be utilized. However, metal oxides can be deposited at low temperatures (less than 100° C.); thus enabling deposition on plastic parts.

A technical effect achieved by the present disclosure is provision of a biocompatible medical device, which is visible in X-rays.

It shall be appreciated by those skilled in the art that the embodiments set forth in the present disclosure may be adapted and combined as desired. The disclosure is thus intended to encompass any possible modifications of the device and the deposition method, recognizable by those of ordinary skill in the art, within a scope of appended claims.

The invention claimed is:

1. A medical device configured as a stent, an intravenous injection tube or a catheter, having at least one surface, wherein at least a part of said surface is coated with a biocompatible layer configured to provide visibility of said device in X-rays, wherein the biocompatible layer comprises at least one metal oxide, the metal oxide being a heavy metal oxide selected from the group consisting of $HfO_2$, $WO_3$, and tantalum oxide, and additionally the biocompatible layer comprises a tungsten carbide, and a metal nitride, selected from the group comprising hafnium nitride, tungsten nitride and tantalum nitride, wherein said tungsten carbide, hafnium nitride, tungsten nitride and tantalum nitride are deposited using plasma-enhanced ALD, wherein said biocompatible layer is an Atomic Layer Deposition (ALD) layer.

2. A method for manufacturing a medical device configured as a stent, an intravenous injection tube or a catheter, comprising: obtaining a medical device, having at least one surface; and depositing a biocompatible layer on at least a part of the surface of said device by Atomic Layer Deposition (ALD), wherein said biocompatible layer is configured to provide visibility of said device in X-rays, wherein the biocompatible layer comprises at least one metal oxide, the metal oxide being a heavy metal oxide selected from the group consisting of $HfO_2$, $WO_3$, and tantalum oxide, and additionally the biocompatible layer comprises a tungsten carbide, and a metal nitride, selected from the group comprising hafnium nitride, tungsten nitride and tantalum nitride, both the metal carbide and metal nitride deposited via plasma-enhanced atomic layer deposition, wherein said biocompatible layer is an Atomic Layer Deposition (ALD) layer.

* * * * *